United States Patent [19]

Papenfuhs

[11] Patent Number: 5,760,258
[45] Date of Patent: Jun. 2, 1998

[54] POLYHYDROXYALKYL-AMIDOAMINE OXIDES

[75] Inventor: Bernd Papenfuhs, Neuötting, Germany

[73] Assignee: Hoechst Aktiengesellschaft, Frankfurt, Germany

[21] Appl. No.: 694,102

[22] Filed: Aug. 8, 1996

[30] Foreign Application Priority Data

Aug. 11, 1995 [DE] Germany ............ 195 29 466.1

[51] Int. Cl.⁶ .................................................. C07C 233/00
[52] U.S. Cl. ..................... 554/66; 554/63; 554/68; 252/351; 252/357
[58] Field of Search ................... 554/63, 66, 68; 252/351, 357

[56] References Cited

U.S. PATENT DOCUMENTS

| 4,077,990 | 3/1978 | Prodo et al. |
| 4,864,060 | 9/1989 | Karalis et al. |

FOREIGN PATENT DOCUMENTS 0367926  5/1990  European Pat. Off.
61-283695  12/1986  Japan.

*Primary Examiner*—Gary Geist
*Assistant Examiner*—Deborah D. Carr
*Attorney, Agent, or Firm*—Connolly and Hutz

[57] ABSTRACT

The amine oxides described correspond to the following formula (1)

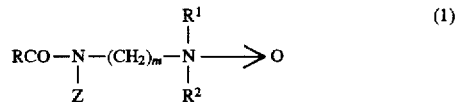

in which RCO is an aliphatic acyl radical having 6 to 22 carbon atoms, Z is a linear polyhydroxyhydrocarbon radical having at least 3 optionally oxyalkylated hydroxyl groups, m is an integer from 1 to 4, $R^1$ is $C_1$ to $C_4$-alkyl or $C_2$ to $C_4$-hydroxyalkyl and $R^2$ is $C_1$ to $C_4$-alkyl or $C_2$ to $C_4$-hydroxyalkyl. The amine oxides and the aqueous, alcoholic or aqueous-alcoholic solutions are prepared by oxidation of corresponding tertiary amine compounds with hydrogen peroxide. The novel amine oxides and their solutions are particularly suitable for the preparation of surface-active compositions for hair and body care.

10 Claims, No Drawings

POLYHYDROXYALKYL-AMIDOAMINE OXIDES

DESCRIPTION

The invention relates to polyhydroxyalkyl-amidoamine oxides, aqueous, alcoholic or aqueous-alcoholic solutions thereof, a process for the preparation of these amine oxides and of their solutions, and the use of the novel amine oxide compounds and solutions thereof.

Amine oxides are valuable compounds from the group of zwitterionic surfactants. Because of their good cleaning power and their other advantageous properties, in particular in respect of foaming properties and skin tolerance, they are employed in the form of liquid formulations above all for cleaning the hair and body. The solvents are in general water, lower alkanols, such as methanol, ethanol, isopropanol, ethylene glycol and/or propylene glycol, or a mixture thereof.

Concentrated to highly concentrated (comprising as little solvent as possible) and at the same time low-viscosity formulations are desirable in respect of storage and transportation costs, further processing and on-the-spot use. The commercially available amine oxide solutions in general have an amine oxide content (active compound content) of less than 30% by weight. Concentrated amine oxide solutions are referred to in the case of an active compound content of 30 to about 35% by weight, and highly concentrated amine oxide solutions at an even higher active compound content.

Amine oxides are in general prepared by oxidation of tertiary amine compounds with hydrogen peroxide in an aqueous or aqueous-alcoholic medium.

In the case of amidoamine oxides in particular, of which the fields of use are above all in the cosmetics and cleaning composition sector (cf. U.S. Pat. No. 4 077 990, JP-A-61-283695 and EP-A-367 926), the solubility is severely limited.

A novel class of amidoamine oxides which are distinguished by a good water-solubility and also low-viscosity formulations having a high amine oxide concentration has now been found.

The amine oxides according to the invention from the group consisting of oxidized polyhydroxyalkylamidoamines correspond to the following formula (1)

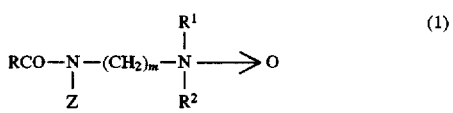
(1)

in which

RCO is an aliphatic acyl radical having 6 to 22 carbon atoms,

Z is a linear polyhydroxyhydrocarbon radical having at least 3 optionally oxyalkylated hydroxyl groups, m is an integer from 1 to 4, $R^1$ is $C_1$ to $C_4$-alkyl or $C_2$ to $C_4$-hydroxyalkyl and $R^2$ is $C_1$ to $C_4$-alkyl or $C_2$ to $C_4$-hydroxyalkyl.

Preferred compounds of the formula (1) according to the invention are those in which RCO is a fatty acyl radical having 8 to 18 carbon atoms, Z is a radical of a sugar-alcohol which is derived from a reducing mono- or disaccharide, in particular from glucose, m is the number 3 and $R^1$ and $R^2$ (identical or different) are methyl, ethyl, propyl or hydroxyethyl.

The following may also be stated regarding RCO and Z: the aliphatic acyl radical RCO, which is preferably the fatty acyl radical mentioned, can be saturated or unsaturated (preferably mono- to triunsaturated). Examples which may be mentioned are the acyl radicals of caprylic, capric, lauric, palmitic, stearic and oleic acid, as well as coconut-acyl, tallow-acyl, preferably hydrogenated tallow-acyl, and the like. The fatty acid radical is often a mixture of two or more acyl groups, for example $C_{12}$ and $C_{14}$-acyl ($C_{12/14}$), $C_{16}$ and $C_{18}$-acyl ($C_{16/18}$) or $C_{12}$ to $C_{18}$-acyl. As already mentioned above, the linear polyhydroxyhydrocarbon radical preferably originates from sugar-alcohols derived from the group consisting of reducing sugars or reducing sugar derivatives. Preferred reducing sugars are the monosaccharides, preferably pentoses and hexoses, and the oligosaccharides, preferably disaccharides and, where appropriate, also trisaccharides. Examples of monosaccharides are glucose, galactose, mannose and talose as hexoses, and arabinose, ribose and xylose as pentoses. Of the monosaccharides, the hexoses are preferred. Examples of oligosaccharides (polysaccharides) are lactose, maltose, maltotriose and the like. Particularly preferred polyhydroxyalkyl radicals originate from reducing hexoses, in particular from glucose (sorbityl radical).

The amine oxides of the formula (1) according to the invention are prepared by oxidation of a tertiary amine compound of the formula (2)

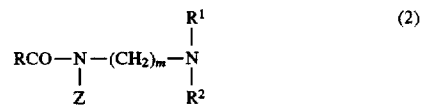
(2)

in which R, $R^1$, $R^2$, Z and m have the meanings given, with hydrogen peroxide in water, a lower alcohol or a mixture of water and a lower alcohol as the solvent.

The reaction of the tertiary amine compound, for example N,N-dimethylaminopropyl-fatty-acyl-glucamide, with hydrogen peroxide is carried out specifically in a manner such that the tertiary amine and the oxidizing agent are employed in a molar ratio of 1:1 to 1.2, preferably 1:1 to 1.15; if appropriate a sequestering agent is added. The solvent can be water, a lower alcohol, preferably methanol, ethanol, isopropanol, ethylene glycol and/or propylene glycol, or a mixture of water and the alcohols mentioned. The amount of solvent (which is introduced into the reaction mixture as such or in the form of solutions of the starting compounds) is in general chosen such that the amine oxide solution obtained after the reaction has an amino oxide content (active compound content) of 30 to about 65% by weight, and preferably 30 to 60% by weight, the percentages by weight being based on the solution. The hydrogen peroxide is used in the form of commercially available aqueous solutions in the range from 20 to 90% by weight. The reaction temperature is in general 60° to 110° C., preferably 70° to 100° C. The oxidation reaction, which proceeds under atmospheric pressure, is maintained until the desired conversion is reached.

The resulting amine oxide solutions comprise the amine oxide according to the invention in a high concentration. It can be obtained in the pure form by separating off the solvent. This is in general unnecessary, because the amine oxides according to the invention are in any case employed above all in solutions.

The amine compounds of the formula (2) given which are required for the preparation of the amine oxides according to the invention and their solutions are advantageously obtained by a) reaction of a polyhydroxyhydrocarbon compound from which the radical Z in formula (1) or formula (2) is derived with an amine of the formula (3)

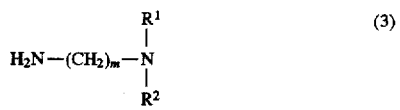

in which m, $R^1$ and $R^2$ have the meanings given, in an aqueous or aqueous-alcoholic medium and in the presence of a hydrogenation catalyst to give the polyhydroxyalkylamine of the formula (4)

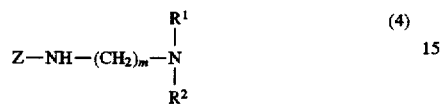

in which Z, m, $R^1$ and $R^2$ have the meanings given, and b) reaction of the product obtained in step a), essentially comprising polyhydroxyalkylamine of the formula (4), with a fatty acid alkyl ester of the formula (5)

in which R has the meaning given and $R^3$ is a $C_1$ to $C_3$-alkyl group, to give the polyhydroxyalkylamidoamine of the formula (2) given. Steps a) and b) are described in more detail below:

Step a) is a reductive amination of a polyhydroxylated compound of the abovementioned type, such as mono- or disaccharide compounds, preferably hexoses, such as glucose, with an amine of the formula (3). The sugar compound and the amine compound are employed in a molar ratio of about 1:1 to 1.2. The solvent, which is preferably water or a mixture of water and a lower alcohol, such as methanol, ethanol and/or isopropanol, is employed in an amount of about 30 to 50% by weight, based on the polyhydroxyalkylamine formed. Catalysts which can be employed are the customary hydrogenation catalysts, such as palladium-on-active charcoal, copper chromite and, in particular, Raney nickel, in an amount of in general 0.01 to 3% by weight, preferably 0.1 to 1% by weight, based on the sugar compound to be aminated. The reductive amination reaction is carried out at a temperature of 40° to 150° C., preferably 50° to 120° C., and under a hydrogen pressure of 10 to 200 bar, preferably 20 to 100 bar. The amino-sugar compound according to formula (4) is obtained in practically quantitative yields.

In step b), the reaction product obtained in step a) (if appropriate after filtering off the catalyst) is acylated with about 1 mol of fatty acid ester of the formula (5) per mole of amino-sugar compound in the presence of a basic catalyst. This is preferably carried out at a temperature of about 60° to 130° C., for example by boiling the reaction mixture under reflux, and leads to the acylated amino-sugar of the formula (2).

The amine oxides according to the invention have unexpectedly good properties. They are soluble in water, lower alcohols or mixtures thereof at room temperature (20° to 25° C.) up to high concentrations. The concentrated to highly concentrated solutions are surprisingly low-viscosity, that is to say are readily flowable, pourable, pumpable and the like, at room temperature. The aqueous, alcoholic or aqueous-alcoholic amine oxide solutions according to the invention are furthermore distinguished by a high clarity (they look water-clear to the human eye) and storage stability. The amine oxides according to the invention are based on regenerating raw materials and are biologically degradable, which is a further advantage of these surfactant compounds with outstanding surfactant properties. On the basis of this profile of properties, the amine oxides and amine oxide solutions according to the invention are advantageously used for the preparation of surface-active compositions for hair and body care.

The invention will now be explained in more detail by examples, in which the abbreviation "DMAP" is dimethylaminopropyl and the abbreviation "GA" is glucamide.

EXAMPLE 1

(DMAP-$C_{12}$-GA-amine oxide)

209.4 g (0.45 mol) of a 96% strength by weight DMAP-$C_{12}$-GA which is free from or low in alkali metal and alkaline earth metal ions, 207.5 g of distilled water and 0.1 g of ethylenediaminetetraacetic acid disodium salt (EDTA) are initially introduced into a four-necked flask fitted with a reflux condenser, stirrer, thermometer and dropping funnel, and are heated to 70° C., while stirring. 45.9 g (0.473 mol) of a 35% strength by weight aqueous hydrogen peroxide solution are then continuously added dropwise in the course of 30 minutes; as a result of the exothermic reaction, the temperature rises to about 80° C. The reaction mixture is now stirred at 75° to 80° C. for a further 5 to 8 hours, during which a highly liquid solution comprising 44% by weight of the corresponding amine oxide of the formula (1) is obtained (97% yield); the residual content of hydrogen peroxide is not more than 0.1% by weight.

EXAMPLE 2

(DMAP-$C_{12/14}$-GA-amine oxide)

| Batch size: | |
| --- | --- |
| 263.0 g (0.55 mol) | of a 95% strength by weight DMAP-$C_{12/14}$-GA which is free from or low in alkali metal and alkaline earth metal ions |
| 255.2 g | of distilled water |
| 0.1 g | of EDTA |
| 56.1 g (0.578 mol) | of a 35% strength by weight aqueous hydrogen peroxide solution |

The reaction is carried out analogously to Example 1. A highly liquid solution comprising 44% by weight of the corresponding amine oxide of the formula (1) is obtained in a yield of 97%.

EXAMPLE 3

(DMAP-$C_{16/18}$-GA-amine oxide)

| Batch size: | |
| --- | --- |
| 138.0 g (0.25 mol) | of a 93% strength by weight DMAP-$C_{16/18}$-GA which is free from or low in alkali metal and alkaline earth metal ions |
| 259.9 g | of distilled water |
| 0.1 g | of EDTA |
| 25.5 g (0.263 mol) | of a 35% strength by weight aqueous hydrogen peroxide solution |

The reaction is carried out analogously to Example 1. A highly liquid solution comprising 30% by weight of the corresponding amine oxide of the formula (1) is obtained in a yield of 96%.

I claim:

1. A polyhydroxyalkyl-amidoamine oxide of the following formula (1)

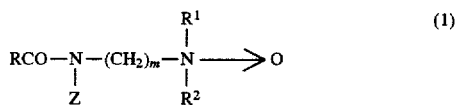

in which

RCO is an aliphatic acyl radical having 6 to 22 carbon atoms,

Z is a linear polyhydroxyhydrocarbon radical having at least 3 optionally oxyalkylated hydroxyl groups, m is an integer from 1 to 4, $R^1$ is $C_1$ to $C_4$-alkyl or $C_2$ to C-hydroxyalkyl and $R^2$ is $C_1$ to $C_4$-alkyl or $C_2$ to $C_4$-hydroxyalkyl.

2. An amine oxide as claimed in claim 1, in which, in formula (1),

RCO is a fatty acyl radical having 8 to 18 carbon atoms,

Z is a radical of a sugar-alcohol which is derived from a reducing mono- or disaccharide, m is the number 3 and $R^1$ and $R^2$ are methyl, ethyl, propyl or hydroxyethyl.

3. An amine oxide as claimed in claim 1, in which, in formula (1),

RCO is a fatty acyl radical having 8 to 18 carbon atoms,

Z is a sorbityl radical, m is the number 3 and $R^1$ and $R^2$ are methyl, ethyl, propyl or hydroxyethyl.

4. A process for the preparation of a polyhydroxyalkylamidoamine oxide as claimed in claim 1, which comprises oxidation of a tertiary amine compound of the formula (2)

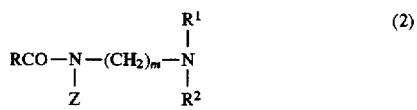

in which R, $R^1$, $R^2$, Z and m have the meanings given, with hydrogen peroxide in water, a lower alcohol or a mixture of water and a lower alcohol as the solvent.

5. The process as claimed in claim 4, wherein 1 to 1.2 mol of hydrogen peroxide are employed per mole of tertiary amine compound and the solvent is employed in an amount such that the amine oxide solution obtained after the reaction has an amine oxide content of 30 to 65% by weight, based on the weight of the solution, and the oxidation reaction is carried out at a temperature from 60° to 110° C.

6. The process as claimed in claim 4, wherein a) a mixture of the solvent and the tertiary amine compound is prepared and this mixture is heated to 70° to 100° C., b) 1 to 1.2 mol of hydrogen peroxide in the form of a 20 to 90% strength by weight aqueous solution per mole of amine are introduced into the heated mixture, the said temperature of 70° to 100° C. being maintained, and c) the reaction mixture obtained in step b) is kept at a temperature of 70° to 100° C. until the desired amine oxide content is reached.

7. An aqueous, alcoholic or aqueous-alcoholic solution of a polyhydroxyalkyl-amidoamine oxide, essentially comprising A) 30 to 65% by weight of at least one compound of the formula (1) in claim 1 and B) water, a lower alcohol or a mixture of water and a lower alcohol as the remainder to make up to 100% by weight.

8. A solution as claimed in claim 7, in which component A) is present in an amount of 30 to 60% by weight.

9. A method for preparing a surface-active composition which comprises incorporating a polyhydroxyalkyl-amidoamine oxide as claimed in claim 1 into a surface-active composition.

10. A method for preparing a surface-active composition which comprises incorporating an aqueous, alcoholic or aqueous-alcoholic solution as claimed in claim 7 into a surface-active composition.

* * * * *